(12) United States Patent
Vladea

(10) Patent No.: US 8,247,623 B2
(45) Date of Patent: Aug. 21, 2012

(54) CATALYTIC PROCESS AND APPARATUS FOR SELECTIVE HYDRATION OF ALKYLENE OXIDE

(75) Inventor: Radu Valentin Vladea, Riyadh (SA)

(73) Assignee: Saudi Basic Industries Corporation, Riyadh (SA)

(*) Notice: Subject to any disclaimer, the term of this patent is extended or adjusted under 35 U.S.C. 154(b) by 1030 days.

(21) Appl. No.: 11/659,530

(22) PCT Filed: Jun. 15, 2005

(86) PCT No.: PCT/CA2005/009926
§ 371 (c)(1),
(2), (4) Date: Feb. 8, 2008

(87) PCT Pub. No.: WO2006/029498
PCT Pub. Date: Mar. 23, 2006

(65) Prior Publication Data
US 2008/0269531 A1    Oct. 30, 2008

(30) Foreign Application Priority Data
Aug. 5, 2004 (EP) .................................. 04018548

(51) Int. Cl.
*C07C 31/18* (2006.01)
*C07C 45/00* (2006.01)
*C07C 27/00* (2006.01)
*C07C 27/26* (2006.01)

(52) U.S. Cl. ......... 568/852; 568/491; 568/867; 568/868
(58) Field of Classification Search .......................... None
See application file for complete search history.

(56) References Cited

U.S. PATENT DOCUMENTS

| | | | |
|---|---|---|---|
| 4,165,440 A | 8/1979 | Kim | |
| 4,222,434 A | 9/1980 | Clyde | |
| 4,277,632 A | 7/1981 | Kumazawa et al. | |
| 4,393,254 A | 7/1983 | Johnson, Jr. et al. | |
| 4,620,044 A | 10/1986 | Chang et al. | |
| 4,937,393 A | 6/1990 | Masuda et al. | |
| 4,967,018 A | 10/1990 | Soo et al. | |
| 5,064,804 A | 11/1991 | Soo et al. | |
| 5,260,495 A | 11/1993 | Forkner | |
| 5,488,184 A | 1/1996 | Reman et al. | |

FOREIGN PATENT DOCUMENTS

| | | |
|---|---|---|
| CA | 2 489 299 A1 | 12/2003 |
| CA | 2 494 849 A1 | 12/2003 |
| CA | 2 502 716 A1 | 4/2004 |
| EP | 0989621 A2 | 3/2000 |
| EP | 1 234 612 A2 | 8/2002 |
| GB | 2 037 607 | 7/1980 |
| GB | 2056043 A | 3/1981 |
| JP | 54128507 A | 10/1979 |
| JP | 61268348 A | 11/1986 |
| JP | 61271229 A | 12/1986 |
| JP | 61271230 A | 12/1986 |
| JP | 61274745 A | 12/1986 |
| JP | 3181338 A | 8/1991 |
| JP | 2001501624 T | 2/2001 |
| JP | 2004509937 T | 4/2004 |
| RO | 103060 B1 | 6/1992 |
| WO | WO98/14419 * | 4/1998 |
| WO | WO 02/34383 A1 | 5/2002 |

OTHER PUBLICATIONS

Machine translation of EP 1234612.*
Chou et al.; "Organic-Inorganic Sol-Gel Coating for Corrosion Protection of Stainless Steel"; Journal of Materials Science Letters; vol. 21; 2002; pp. 251-255.
European Search Report; European Application No. 04018548; Date of Completion: Nov. 24, 2004; 1 Page.
Ono et al.; "Improvement of Corrosion Resistance of Metals by an Environmentally Friendly Silica Coating Method"; Journal of Sol-Gel Science and Technology; vol. 29; 2004; pp. 147-153.
International Search Report; International Application No. PCT/CA2005/000926; International Filing Date: Jun. 15, 2005; Date of Mailing: Oct. 13, 2005; 3 Pages.
Written Opinion of the International Searching Authority; International Application No. PCT/CA2005/000926; International Filing Date: Jun. 15, 2005; Date of Mailing: Oct. 13, 2005; 5 Pages.

* cited by examiner

*Primary Examiner* — Porfirio Nazario Gonzalez
*Assistant Examiner* — James Meadows
(74) *Attorney, Agent, or Firm* — Cantor Colburn LLP

(57) ABSTRACT

The present invention relates to an apparatus for the catalytic production of alkylene glycol from alkylene oxide, comprising: a reactor having at least one heat exchange element incorporated therein, wherein a catalyst for the hydration of alkylene oxide to alkylene glycol is coated on the outer surface of the heat exchange element. The present invention also relates to a process utilizing such an apparatus.

28 Claims, 2 Drawing Sheets

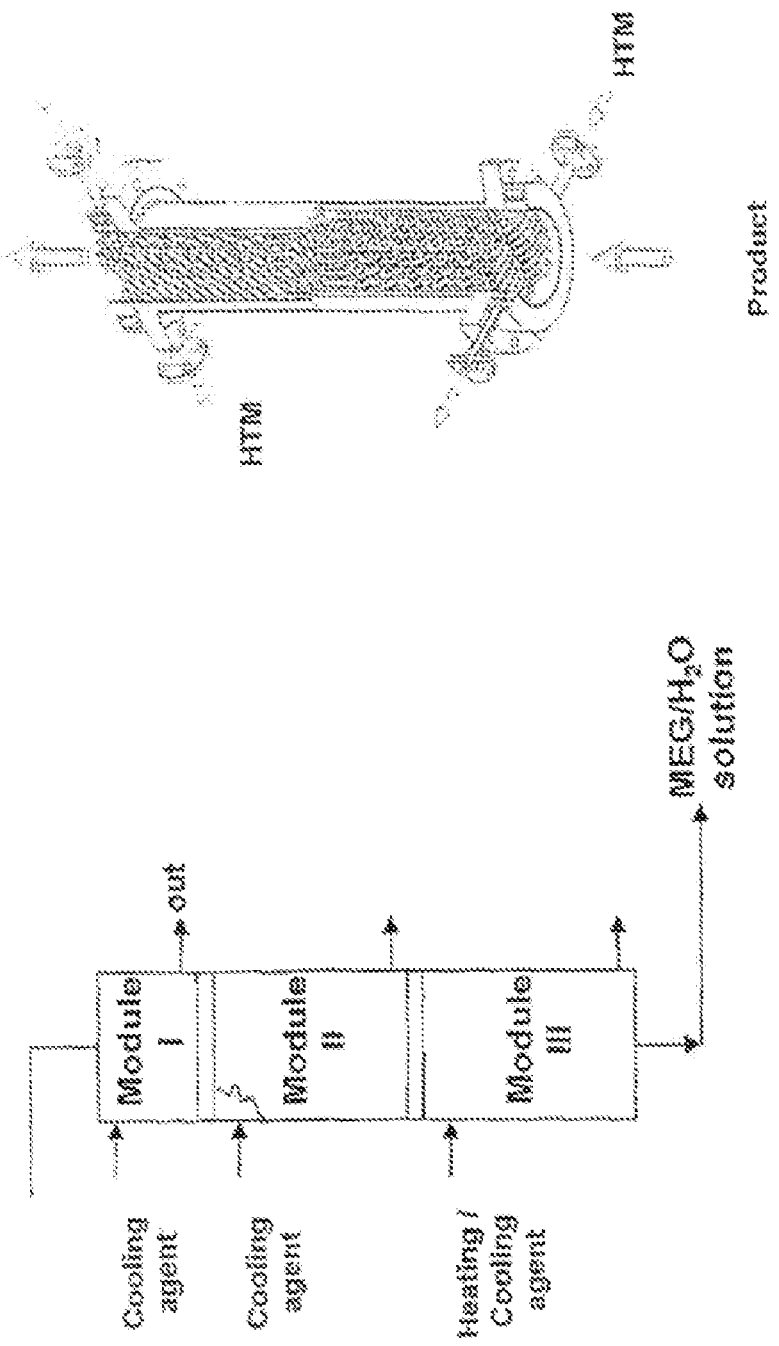
Fig. 1 – Plug flow reactor with modulated temperature, residence time and catalyst loading profiles.
Fig. 2 – Cutaway of a Sulzer SMR reactor

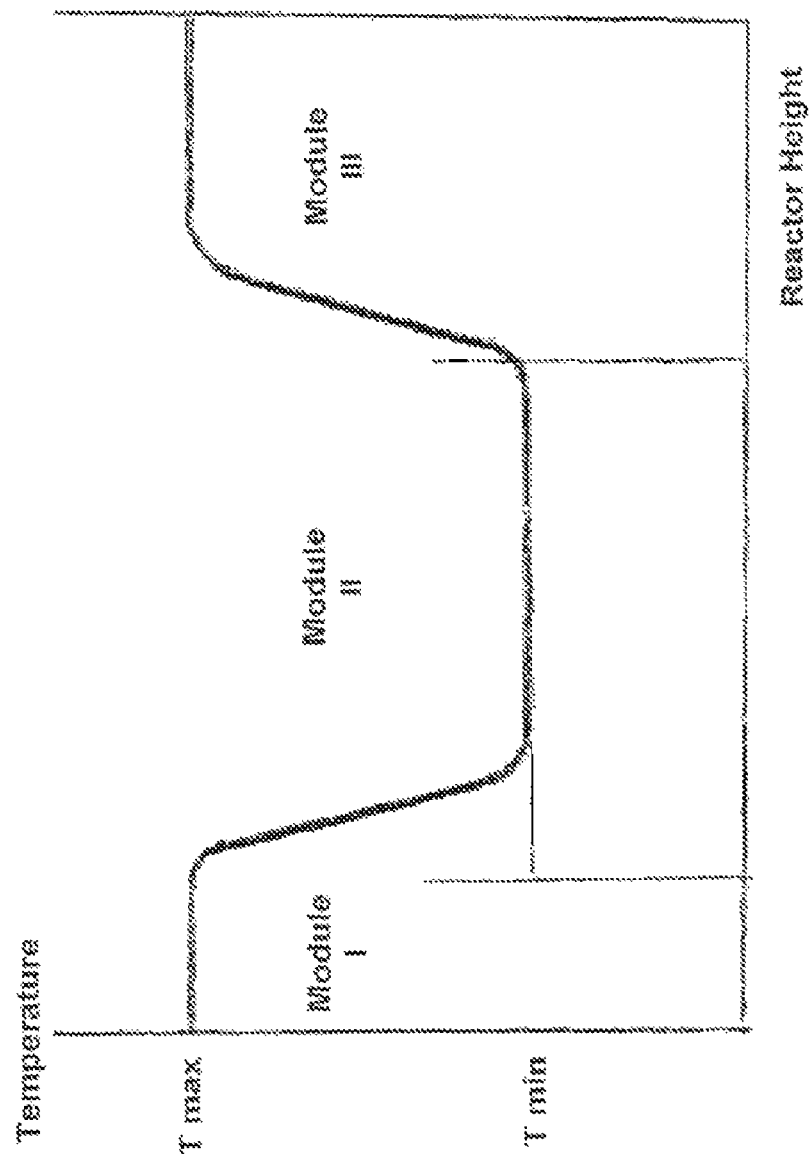
Fig. 3 Temperature profile along the reactor height.

CATALYTIC PROCESS AND APPARATUS FOR SELECTIVE HYDRATION OF ALKYLENE OXIDE

BACKGROUND

The present invention is related to a catalytic process and apparatus for the selective hydration of alkylene oxides.

The production of alkylene glycol, for example ethylene glycol, by thermal or catalytic hydration of the respective alkylene oxide is a well known reaction. Temperature, pressure, residence time, reactor design and the ratio of reactants are adjusted to optimize the thermal process. The catalytic processes add the nature of catalyst to the above mentioned process variables. A large number of catalysts have been used including anionic or cationic ion exchange resins. U.S. Pat. No. 4,937,393 discloses the use of sodium formate or trimethylamine acetate plus acetic acid as hydration catalyst. JP 61-271229 teaches the use of sodium glutamate. JP 61-271230 teaches the use of anthranilic acid as catalyst. U.S. Pat. No. 4,620,044 discloses the use of a bed of zeolite ZSM-5,H-form, as catalyst. U.S. Pat. No. 4,277,632 describes the use Mo or W metal or salts as catalysts. JP 54-128507 discloses the use of sodium tungstate, whereas U.S. Pat. No. 5,488,184 discloses the use of strongly basic ion exchange resin of the quaternary ammonium type, exchanged with bicarbonate as catalyst. Further, U.S. Pat. No. 4,165,440 teaches the use of fluorinated acid exchange resin deposited on a silica support as catalyst. U.S. Pat. No. 4,393,254 mentions the hydration catalyzed by partially amine-neutralised sulfonic acid resins. U.S. Pat. No. 5,260,495 discloses the use of hydrotalcite catalyst which contains Ni and Al, a large organic anion such as terephthalate and a metalate such as niobate or vanadate as catalyst. Finally, U.S. Pat. No. 5,064,804 and U.S. Pat. No. 4,967,018 disclose similar hydrotalcite catalysts.

Some of the prior art processes disclosed above show low selectivities and conversions, being sometimes even lower than the values reported for thermal processes. Further, other prior art references disclose very long contact times, i.e. low liquid hourly space velocity values (LHSV), which impose the use of high amounts of catalyst. Further, no reference discloses the pressure drops induced by such high volume of catalyst. In the prior art processes, an efficient dissipation of reaction heat and, implicitly, good temperature control over the reaction zone is complicated.

The hydration of alkylene oxide (for example ethylene oxide (EO)) is a highly exothermic reaction. The first reaction is a typical hydration while the consecutive ones are reactions of alkylation at oxygen of monoethylene glycol with ethylene oxide; the activation energy ($E_a$) for the hydration reaction is lower than that for the consecutive reactions, therefore a decrease of the reaction medium temperature will decrease the chance for consecutive reactions.

To avoid the consecutive alkoxylation reactions, it is also advisable to run the process with very short residence time still maintaining an almost total conversion of alkylene oxide. To fulfill this requirement, a highly active catalyst is required. The use of a highly or superactive catalyst enables one to run the process at lower temperatures, thus hampering those consecutive reactions with higher activation energies, which are generating side-products and are lowering the selectivity of the process. In the meantime, by employing such high or superactive catalysts, one can achieve almost total conversions at ultra short contact (residence) times.

SUMMARY

It is therefore the object of the present invention to provide an apparatus for the catalytic production of alkylene glycol overcoming the disadvantages of the prior art, especially to provide a process utilizing the apparatus showing high activity at lower temperature, very high liquid velocities and short contact times, low pressure drops and high flow rates, small amounts of catalysts required per unit of product.

The object is achieved by an apparatus for the catalytic production of alkylene glycol from alkylene oxide, comprising: a reactor having at least one heat exchange element incorporated therein, wherein a catalyst for the hydration of alkylene oxide to alkylene glycol is coated on the outer surface of the heat exchange element.

It is preferred that the catalyst is coated on the surface of the heat exchange element in a thickness in a range of about 20 nm to about 300 µm, preferably about 50 nm to about 100 µm.

Most preferably, the reactor is a tubular reactor.

In a preferred embodiment, the heat exchange element is in the form of a hollow tube and several heat exchange elements are in the form of a bundle of hollow tubes, preferably spiraled coils It is also alternatively preferred that the heat exchange elements are in the form of corrugated duplex sheets of a sandwich-type shape.

Mostly preferred the heat transfer fluid may circulate in the heat exchange elements.

It is also preferred that the heat transfer fluid is water.

Preferably, the catalyst comprises a solid superacid or a solid superbase.

Another embodiment of the invention is that the catalyst comprises fluoroalkyl sulfonic acid resins or any ionomers with a Hammet $H_0$ acidity about −12, heteropolyacids, zeolites or mixtures thereof.

A preferred embodiment is characterized in that the catalyst comprises a perfluorinated ion-exchange polymer with pendant sulfonic acid groups having an acid strength from about 0.4 meq·$H^+g^{-1}$ to about 0.9 meq·$H^+g^{-1}$, preferably between 0.5 and 0.7 meq·$H^+g^{-1}$.

It is also preferable that the catalyst comprises alumina, zeolites or silicates doped with alkaline hydroxides and metals belonging to group I or II of the periodic table of elements.

Most preferred, the catalyst is coated on the surface of the heat exchange element with a binding material.

Mostly preferred, the binding material is selected from the group of polymers, macroporous polymers, colloidal silica and the like.

In a most preferred embodiment of the invention, the heat exchange element acts as a mixer, preferably a static mixer.

In a further embodiment the reactor is connected to at least one device for supplying heat transfer fluid to the heat exchange element and at least one device for leading away heat transfer fluid from the heat exchange element.

It is preferred that the reactor is connected to at least one device for supplying a feed containing alkylene oxide and at least one device for leading away product containing alkylene glycol from the reactor.

Still preferred, the reactor comprises more than one module, each module comprises one or more heat exchange elements.

In one preferred embodiment, each module has a specific height, is held at a specific temperature and has a specific amount of catalyst loading Another object of the invention is achieved by a process for the production of alkylene glycol from allylene oxide utilizing the apparatus according to the invention, wherein feed containing a solution of alkylene oxide and water is contacted with the catalyst coated on the outer surface of the heat exchange element.

Preferably, the weight ratio of water to allylene oxide in the feed is between about 1:1 and 100:1, preferably between about 1.5:1 and about 20:1 and most preferably between about 2:1 and about 15:1.

Most preferably the temperature at which the feed is contacted with the catalyst is in the range of from about 20° C. to about 115° C., preferably from about 50° C. to about 110° C., and more preferably from about 75° C. to about 110° C.

Also preferably, the contact time between the catalyst and the feed is in the range of about 0.01 seconds to 1 minute, preferably between 0.05 seconds and 30 seconds.

Finally, it is preferred that the alkylene oxide is selected from the group consisting of ethylene oxide propylene oxide, butylene oxide or mixtures thereof.

Surprisingly, the process according to the present invention utilizing the inventive apparatus overcomes the drawbacks of the prior art. In detail, the apparatus and the process provide several outstanding features: high activity at low temperature, very high liquid velocities, therefore very short contact times, very low pressure drops at high flow rates, very small amounts of catalysts required per unit of product, very high throughput, therefore a small reaction volume is required. Finally, all these features lead to high process selectivity and low operating and investment costs.

The inventive apparatus and process enable that the high reaction heat release due to high reaction rates may be efficiently dissipated from the apparatus in order to accurately control the temperature within the reaction zone and to avoid any non-selective thermal reactions. As high reaction rates determine high radial and axial concentration and temperature gradients, which are deleterious for the reaction system, a very efficient motionless mixing is provided utilizing the heat exchange elements as a mixer, preferably a static mixer. The heat exchangers therefore provide a good mixing effect and a very efficient reaction heat removal.

Most preferably, a tubular reactor is used in the inventive process to ensure the best plug-flow pattern without any back-mixing effects for the streams, an essential condition for good selectivity.

It is essential for catalysts used in the inventive process to have appropriate porosity and hydrophobic properties. The catalyst may be coated on the outer surface of the heat transfer element per se or by using a binding material being chemically inert and resistant to the reaction environment. The catalyst can be bonded by any of the methods known in the art, such as in-situ crystallization on support, dip coating in appropriate solutions or suspensions of active components in a solution or a melted polymer, dry gel conversion, seed film method on a polymer pre-coated surface.

Preferably, the heat exchange elements are multiple spiraled coils. However, the heat exchanger can also be made of corrugated duplex sheets of a sandwich-type shape through which the heat transfer fluid can circulate. These elements may also act as mixing elements enabling a plug flow pattern along the reaction zone.

The catalyst layer can be loaded on the metallic surface by any physical or chemical deposition method, such as dip-coating, sputtering, metal-organic chemical vapor deposition or the like. In all cases, however, techniques are needed to clean the support surface prior deposition.

Additional features and advantages of the subject-matter of the present invention will become apparent from reading the following detailed description of examples for carrying out a process for the production of alkylene glycol from alkylene oxide utilizing an inventive apparatus in combination with the drawings, wherein

BRIEF DESCRIPTION OF THE DRAWINGS

FIG. 1 shows a reactor for use in an apparatus according to one embodiment of the present invention, comprising three modules for carrying out the inventive process;

FIG. 2 shows a cutaway through one module given in FIG. 1; and

FIG. 3 shows a graph illustrating the temperature profile along the height of the reactor according to FIG. 1.

DETAILED DESCRIPTION

Preferably, a reactor for use in an apparatus for the catalytic production of alkylene glycol from alkylene oxide according to the present invention may consist of three modules connected in series, as illustrated in FIG. 1. FIG. 1 shows a plug-flow reactor with modulated temperature, residence time and catalyst loading profiles. Each module has its own height, temperature and catalyst loaded on cooling/heating elements as shown in FIG. 1. The stream of starting material containing alkylene oxide flows downwardly, i.e. the starting stream flows at first into module I, enters module II and finally enters module III, yielding alkylene glycol in the product stream. Each module, as shown in FIG. 1, may comprise one or more cooling/heating units.

An example of such a heating/cooling unit in a reactor is shown in FIG. 2, wherein FIG. 2 illustrates two such units within one module. Heat transfer medium (HTM) may be introduced into each element and may be discharged.

Preferably, the residence time—being proportional with the reactor height—may have different distributions along each module, for example, in percentage of a total residence time: 30% (module I)-60% (module II)-10% (module III).

Also, the catalyst loading may be distributed following a certain profile imposed by catalyst nature, temperature and residence time profiles. Preferably, a less amount of catalyst is in the first module, more catalyst than in the first module is in the second module, and less or equal amount of catalyst compared to the second module is in the third one. For example, in percentage of total catalyst loading: 20% (module I)-40% (module II)-40% (module III), or 30% (module I)-40% (module II)-30% (module III).

Further, the temperature profile along the reactor height, wherein the reactor height is build up by three modules I-III, may be varied between a minimum temperature and a maximum temperature, as disclosed in FIG. 3.

Use of different modules in the reactor having different height, temperature and catalyst loading enables fine-tuning of the inventive process to obtain alkylene glycol in desired conversions and selectivities.

EXAMPLES

The following examples are intended to be illustrative for this invention only. They are, of course, not to be taken in anyway as limiting on the scope of the invention. Numerous changes and modifications can be made with respect to the invention.

Example 1

An exemplary process involves contacting a solution of ethylene oxide and water with a catalyst, preferably a super-acid, coated on the metallic outer surface of a heat exchanger element located in a tubular reactor. The temperature at which the ethylene oxide/water solution is contacted with the catalyst is in a range of from 20° C. to about 115° C., preferably from about 50° C. to about 110° C., and more preferably from about 75° C. to about 105° C. The weight ratio of water to ethylene oxide in the solution contacting the catalyst is between about 1:1 and 100:1, preferably between 1, 5:1 to 20:1 and most preferably between about 3:1 to about 15:1.

The heat exchange element is preferably a multiple spiraled coil, which has been coated after cleaning its surface with a thin film (about 100 nm) of perfluorinated ion-exchange polymer having a backbone structure similar to TEFLON® (polytetrafluoroethylene) with pendant sulfonic acid groups resulting in acid strengths from about 0.4 meq·H$^+$ g$^{-1}$ to about 0.9 meq·H$^+$g$^{-1}$, preferably between 0.5 and 0.7 meq·H$^+$g$^{-1}$. A solution of 3-5% polymer in mixture of lower aliphatic alcohols and water has been used.

The contact time between the catalyst and the aqueous solution depends on the ethylene oxide concentration in the aqueous solution and the density of CF2SO3H groups on the catalyst backbone. The contact times were in a range of 0.01 seconds to 1 minute, preferably between 0.5 seconds and 30 seconds. The reaction temperature has been controlled within 0.2° C.

A conversion of 99.9% of ethylene oxide and a selectivity of 99.5% of ethylene glycol was achieved.

Example 2

Stainless steel metallic coils of a motionless mixer-heat exchanger such as SMR sold by Sulzer Chemtech Ltd, P.O. Box 65 CH-8404 Winterthur, Switzerland, have been cleaned following usual procedure: spraying with an oil-in-water emulsion followed by immersion into an alkaline solution of borax at 60° C. and a thorough rinse with deionized (DI) water. In order to ensure a tight bond and good adhesion between the substrate surface and the sol-gel coating the procedure followed the technique mentioned in the open literature (T. P. Chou, C. Chandrasekaran, S. Limmer, C. Nguyen, G. Z. Cao, Journal of Materials Science Letters, 21, 251, 2002). The substrate was exposed to surface hydroxylation at an elevated temperature by immersing it into a solution mixture of 30% hydrogen peroxide ($H_2O_2$) and concentrated sulfuric acid with a 30:70 volume ratio, at 90° C. for 30 minutes. A DI water rinse was used to wash excess solution remaining and the substrate was then stored in DI water to preserve the hydroxyl groups on the surface.

Using a dip-coater such as the one sold by Chemat Technology Inc, 9036 Winnetka Avenue, Northridge, Calif. 91324, U.S.A., model 201, the SMR's coils were dipped into the sol at a constant speed of 140 mm/min, immersed into the sol for 1.5 min, and then withdrawn at the same speed. The coated coils were air-dried for 1 min and placed in a furnace at 300° C. for approximately 30 min at a heating/cooling rate of 5° C./min. A layer of 0.2 μm in thickness has been obtained.

The sol was prepared by blending a sol of acidic cesium salt of a heteropolyacid (HPA), dodecatungstophosphoric acid with formula $CS_{2.5}H_{0.5}PW_{12}O_{40}$, and a silica-based organicinorganic hybrid sol in a ratio of 60:40 by weight of solid components.

The silica sol with particle sizes of the order of less than 100 nm has been prepared with an acid-catalyzed, two-step hydrolysis-condensation process. An organic monomer, 3-methacryloxypropyl-trimethoxysilane, has been added to the silica precursor tetraethyl-orthosilicate (TEOS) (Fluka, reagent grade) to control the flexibility and density of the sol-gel network. The preparation followed the recipe of S. Ono, H. Tsuge, Y. Nishi, and S. Hirano, J. Sol-Gel Science & Technology, 29 (3) 147, (2004).

The HPA sol has been prepared using the titration procedure indicated by T. Okuhava, H. Watanabe, T. Nishimura, K. Inumaru, and M. Misono, Chem. Mater. 12, 2230 (2000). After aging, the colloid suspension of HPA has been added, under vigorous stirring, to the silica sol.

The SMR unit, coated with catalyst, was connected in an experimental setup for ethylene oxide hydration. The ethylene oxide solution ($H_2O$:EO=2.5:1 by weight) has been stored at room temperature in a closed vessel under a pure nitrogen blanket. The solution has been fed into the reactor using a metering pump via a preheater (80° C.). The flow rate was 1 liter/second, the temperature was kept at 110±0.5° C., and the pressure was 10 bar.

The pressure drop over the reaction zone was 0.03 bar. Conversion was 99.9% with a selectivity of 97.5% monoethylene glycol. The catalytic system has been tested for 280 hours and showed no alteration of its performance.

Example 3

A heteropolyacid with a formula $Cs_{2.1}H_{0.9}PW_{12}O_{40}$, prepared as in Example 2, has been used in identical conditions as in Example 2. Conversion was 96% with a selectivity of 99%.

Example 4

The heteropolyacid (CsHPA) $Cs_{2.5}H_{0.5}PW_{12}O_{40}$ prepared as in example 2, separated from the colloidal solution as particles with sizes around 100 nm was admixed into a chloroform solution of polyphenylene oxide (PPO) [poly-2,6-dimethyl-1,4-phenylene oxide], Aldrich Chemical Co, reagent grade, in a ratio 80:20 by weight CsHPA:PPO. The SMR coils were dipcoated with the resulting slurry and dried at 60° C.

The catalytic system has been used at 100° C., pressure 9 bar, flow rate 0.08 liter/second aqueous solution of EO with a ratio $H_2O$:EO=5:1 by weight.

Conversion was 99.6% and selectivity 99%. No decay in activity and selectivity has been noted after 200 hours onstream.

The features disclosed in the foregoing description or in the claims may, both separately and in any combination thereof, be material for realizing the invention in diverse forms thereof.

The invention claimed is:

1. A process for the production of alkylene glycol from alkylene oxide utilizing an apparatus comprising a reactor having a heat exchange element incorporated therein, wherein feed containing a solution of alkylene oxide and water is contacted with a catalyst for the hydration of alkylene oxide to alkylene glycol which is coated on the outer surface of the heat exchange element and the catalyst comprises a solid superacid or a solid superbase.

2. The process according to claim 1, wherein the catalyst is coated on the surface of the heat exchange element in a thickness in a range of about 20 nm to about 300 μm.

3. The process according to claim 1, wherein the catalyst is coated on the surface of the heat exchange element in a thickness in a range of about 50 nm to about 100 μm.

4. The process according to claim 1, wherein the reactor is a tubular reactor.

5. The process according to claim 4, wherein the heat exchange element is in the form of a bundle of hollow tubes.

6. The process according to claim 5, wherein the bundle of hollow tubes are spiraled coils.

7. The process according to claim 1, wherein the heat exchange elements are in the form of corrugated duplex sheets of a sandwich-type shape.

8. The process according to claim 1, additionally comprising heat transfer fluid circulating in the heat exchange elements.

9. The process according to claim 8, wherein the heat transfer fluid is water.

10. The process according to claim 1, wherein the catalyst comprises fluoroalkyl sulfonic acid resins or any ionomers with a Hammet $H_0$ acidity about −12, heteropolyacids, zeolites or mixtures thereof.

11. The process according to claim 10, wherein the catalyst comprises a perfluorinated ion-exchange polymer with pendant sulfonic acid groups having an acid strength from about 0.4 meq·$H^+g^{-1}$ to about 0.9 meg·$H^+g^{-1}$.

12. The process according to claim 1, wherein the catalyst comprises alumina, zeolites or silicates doped with alkaline hydroxides and metals belonging to group I or II of the periodic table of elements.

13. The process according to claim 1, wherein the catalyst is coated on the surface of the heat exchange element with a binding material.

14. The process according to claim 13, wherein the binding material is selected from the group consisting of polymers, macroporous polymers and colloidal silica.

15. The process according to claim 1, wherein the heat exchange element acts as a mixer.

16. The process according to claim 15, wherein the heat exchange element acts as a static mixer.

17. The process according to claim 1, wherein the reactor is connected to at least one device for supplying heat transfer fluid to the heat exchange element and at least one device for leading away heat transfer fluid from the heat exchange element.

18. The process according to claim 1, wherein the reactor is connected to at least one device for supplying a feed containing alkylene oxide and at least one device for leading away product containing alkylene glycol from the reactor.

19. The process according to claim 1, wherein the reactor comprises more than one module, each module comprises one or more heat exchange elements.

20. The process according to claim 1, wherein the weight ratio of water to alkylene oxide in the feed is between about 1:1 and 100:1.

21. The process according to claim 20, wherein the weight ratio of water to alkylene oxide in the feed is between about 1.5:1 and about 20:1.

22. The process according to claim 21, wherein the weight ratio of water to alkylene oxide in the feed is between about 2:1 and about 15:1.

23. The process according to claim 1, wherein the feed is contacted with the catalyst at a temperature in the range of from about 20° C. to about 115° C.

24. The process according to claim 23, wherein the temperature is from about 50° C. to about 110° C.

25. The process according to claim 24, wherein the temperature is from about 75° C. to about 110° C.

26. The process according to claim 1, wherein the catalyst and the feed is contacted at a contact time in the range of about 0.01 seconds to 1 minute.

27. The process according to claim 26, wherein the contact time is between 0.05 seconds and 30 seconds.

28. The process according to claim 1, wherein the alkylene oxide is selected from the group consisting of ethylene oxide propylene oxide, butylene oxide, and mixtures thereof.

\* \* \* \* \*